United States Patent
Shafer (10) Patent No.: US 6,925,815 B2
(45) Date of Patent: Aug. 9, 2005

(54) ROBOT COMPATIBLE CRYSTAL WORKSITE SUITE

(75) Inventor: Richard E. Shafer, Webster, TX (US)

(73) Assignee: Oceaneering International, Inc., Houston, TX (US)

( * ) Notice: Subject to any disclaimer, the term of this patent is extended or adjusted under 35 U.S.C. 154(b) by 0 days.

(21) Appl. No.: 10/349,234

(22) Filed: Jan. 22, 2003

(65) Prior Publication Data

US 2004/0008814 A1 Jan. 15, 2004

Related U.S. Application Data

(60) Provisional application No. 60/350,920, filed on Jan. 23, 2002.

(51) Int. Cl.$^7$ ................................................. F25B 19/00
(52) U.S. Cl. ........................................................ 62/51.1
(58) Field of Search ................................ 62/45.1, 51.1, 62/157, 231, 451

(56) References Cited

U.S. PATENT DOCUMENTS

| | | | | |
|---|---|---|---|---|
| 4,363,783 A | * | 12/1982 | Sitte | 422/63 |
| 4,388,814 A | * | 6/1983 | Schilling | 62/62 |
| 4,790,141 A | * | 12/1988 | Glascock | 62/78 |
| 4,958,498 A | * | 9/1990 | Brothers | 62/51.1 |
| 5,168,793 A | * | 12/1992 | Padamsee | 99/279 |
| 5,503,060 A | * | 4/1996 | Morecroft et al. | 99/295 |
| 6,253,955 B1 | * | 7/2001 | Bower | 221/150 R |
| 6,404,849 B1 | * | 6/2002 | Olson et al. | 378/79 |
| 6,701,743 B1 | * | 3/2004 | Durst et al. | 62/457.9 |

* cited by examiner

Primary Examiner—William C. Doerrler
(74) Attorney, Agent, or Firm—Duane Morris LLP (57) ABSTRACT

The present invention is directed to a robot compatible crystal worksite suite comprising a unique dewar, a plurality of magazines, a plurality of cryo-pins (that mount crystals to be transferred from the dewar for crystallography study) adapted to be placed into the magazines and a programmed controller to provide the operational sequence necessary to remove the frozen mounted crystals from the dewar to an instrument or a goniometer for the x-ray diffraction of the crystals.

5 Claims, 10 Drawing Sheets

ROBOT COMPATIBLE CRYSTAL WORKSITE SUITE

RELATED APPLICATION

This application is based on provisional application No. 60/350,920, filed Jan. 23, 2002 now abandoned, entitled "Crystal Carrier Magazine System for Use in Crystallography Applications".

FIELD OF THE INVENTION

The present invention is directed to a suite of apparatus used in handling crystals for x-ray crystallographic analysis. More specifically, the suite of apparatus includes a unique dewar, a plurality of magazines, a plurality of cryo-pins (that mount crystals to be transferred from the dewar for crystallography study) adapted to be placed into the magazines and a programmed controller to provide the operational sequence necessary to remove the frozen mounted crystals from the dewar to an instrument or a goniometer for the x-ray diffraction of the crystals.

BACKGROUND OF THE INVENTION

U.S. Pat. No. 6,408,047 discloses a method of performing x-ray crystallography on samples by using a robot to transfer the samples to a goniometer. This patent is incorporated herein by reference. The patent discloses the general system that the present invention is directed to but does not disclose a worksite suite as disclosed herein.

U.S. Pat. No. 6,404,849 discloses a method and apparatus for mounting a crystal sample for x-ray crystallographic analysis. This patent is incorporated herein by reference. The patent discloses the general system that the present invention is directed to but does not disclose a worksite suite as disclosed herein.

While both patents disclose the general environment of the present invention, the present invention is directed to a worksite suite suitable for use when using a robot to provide the high throughput, automated crystallography methods disclosed in the patents.

SUMMARY OF THE INVENTION

The present invention is directed to a robot compatible crystal worksite suite comprising a unique dewar, a plurality of magazines, a plurality of cryo-pins (that mount crystals to be transferred from the dewar for crystallography study) adapted to be placed into the magazines and a programmed controller to provide the operational sequence necessary to remove the frozen mounted crystals from the dewar to an instrument or a goniometer for the x-ray diffraction of the crystals.

DESCRIPTION OF THE INVENTION

Figure 1:
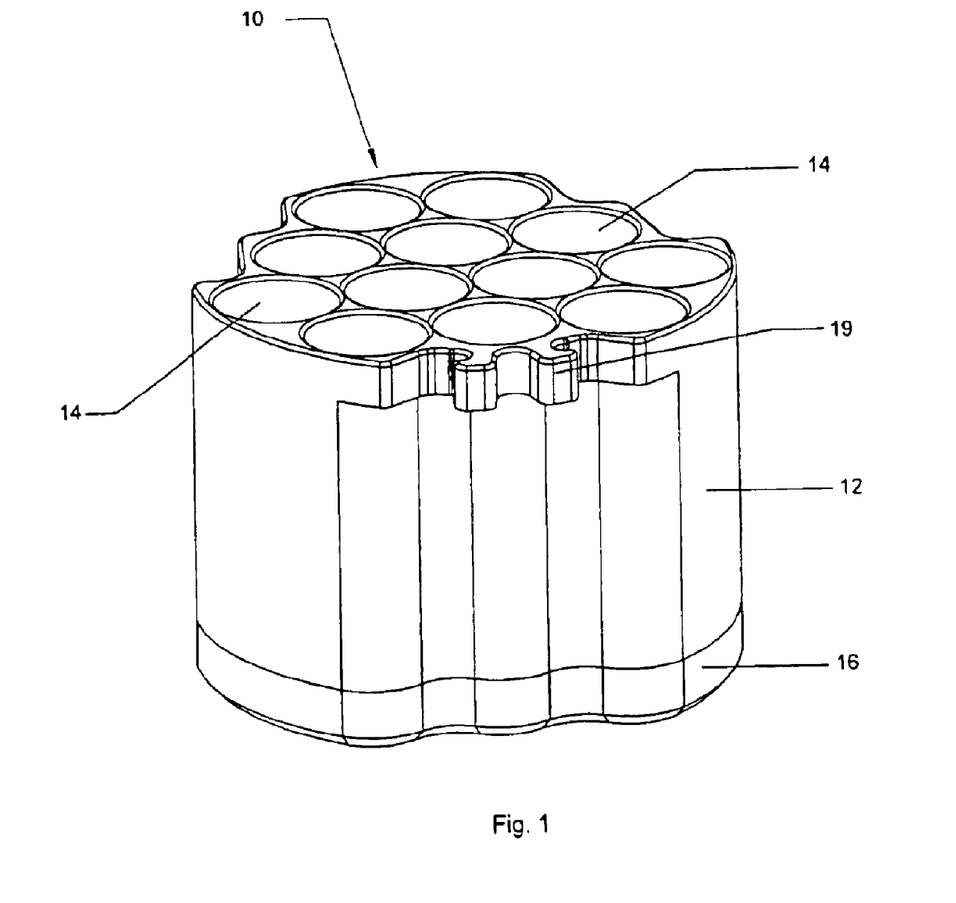
FIG. 1 is a magazine of the present invention.
Figure 2:
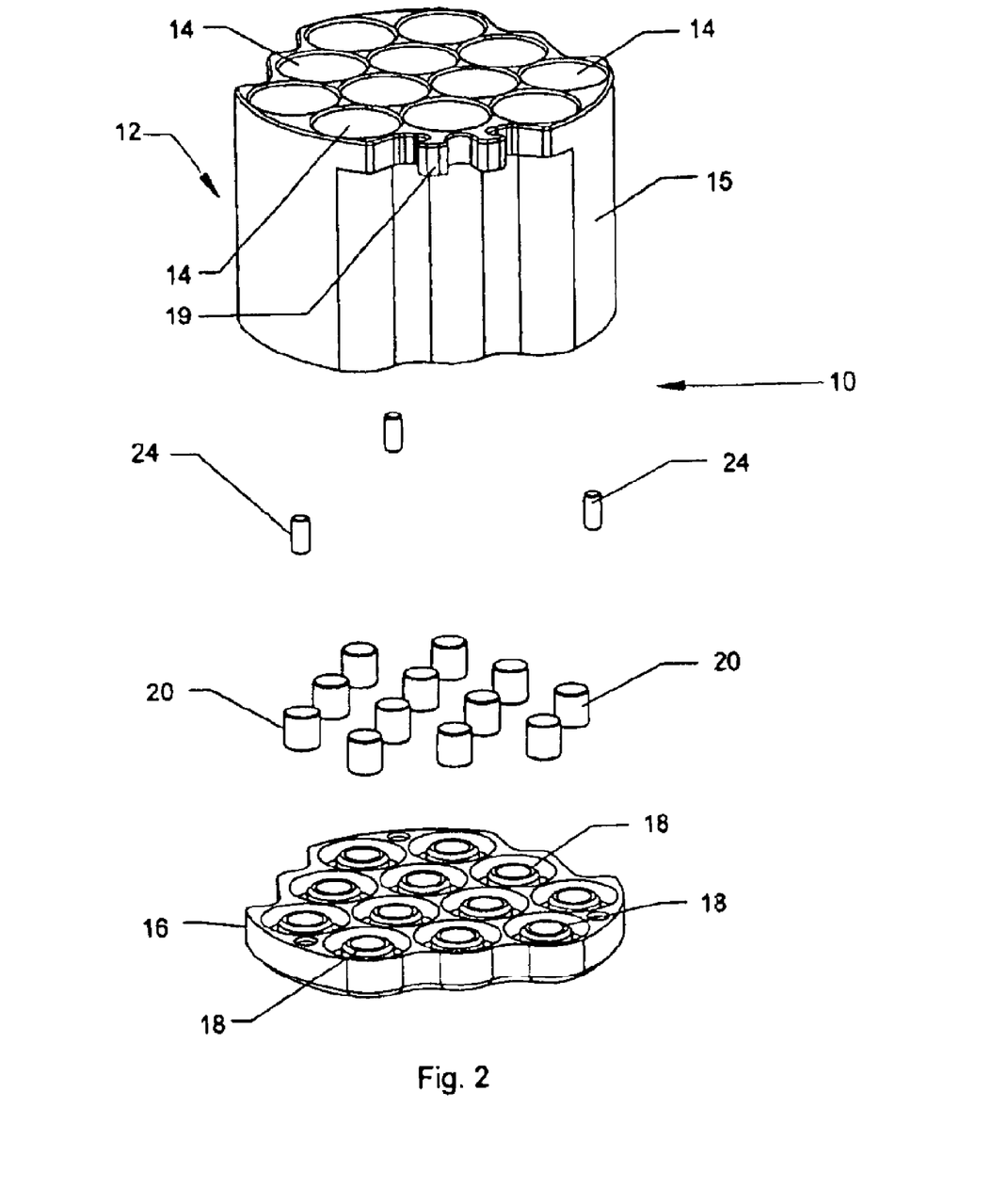
FIG. 2 is an exploded view of a magazine of the present invention.
Figure 3:
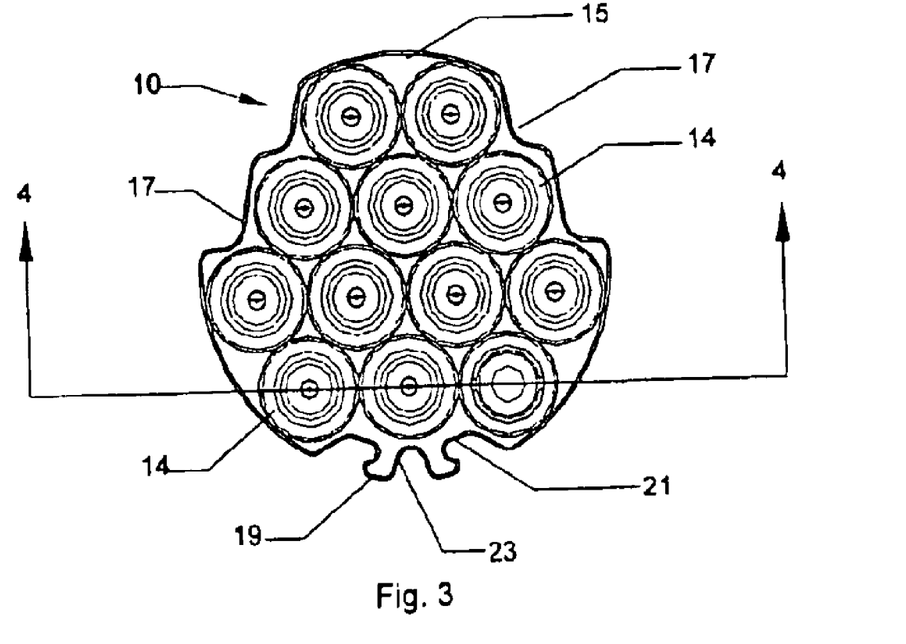
FIG. 3 is a top view of a magazine of the present invention.

The central component of the suite of apparatus of the present invention used in handling crystals for x-ray crystallographic analysis is a multi-position magazine. The magazine is used for precisely locating, protecting and transferring batches of crystals that require cryogenic storage and handling. The magazine 10 is constructed from two parts, as shown in FIG. 1 and FIG. 2. The top part 12 of magazine 10 has a plurality of cylinders 14, specifically shown are twelve (12) cylinders; however the exact number may vary. The cylinders 14 are held by an outer member 15 that is essentially configured as a circle. The lower part 16 of magazine 10 has the same number of location bosses 18 as cylinders 14 that are positioned to be centered in the corresponding cylinder. In each location boss 18 is a magnet 20. The strong magnets 20 are held in place with epoxy to hold the cryo-pin 30, a product of Hampton Research having a ferrous base 34 (see FIG. 4), securely on the location bosses 18. The magnets 20 also hold the magazine 10 securely on a ferrous work surface during crystal manipulation. The upper part 12 and lower part 16 of magazine 10 are held together with epoxy and pressed spring pins 24. Referring now to FIG. 3, the outer member 15 conforms to surface of the cylinders 14 to provide guides 17 the gross location of the magazine 10. On one surface of outer member 15, a member 19 is in a form to provide tabs 21 for the forceps grasping tool 40 and a slot 23 for a locking pin, described hereinafter.

Figure 4:
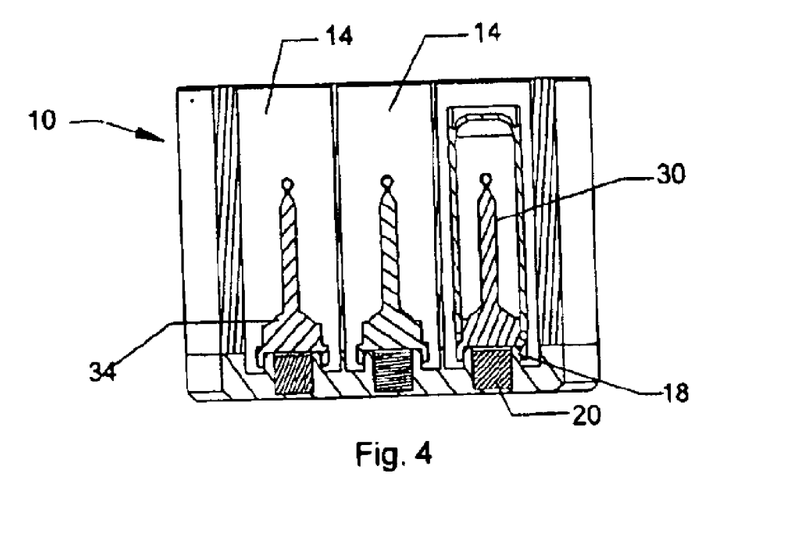
FIG. 4 is a cross-sectional view of a magazine of the present invention along line 4—4 of FIG. 3.

The magazine 10 described in FIGS. 1–4 provides a device for protecting and transferring twelve crystals each mounted on a cryo-pin 30. The cryo-pins 30, that hold the frozen crystals, are seated in the cylinders 14 of the magazine 10 as shown in FIG. 4. The cylinders 14 hold liquid nitrogen and keep the cryo-pins 30 submerged in the liquid nitrogen while the magazine 10 is transfer from one dewar to another. The cylinders 14 also protect the crystals and pins 30, which are held to the boss 18 on the bottom part 16 of the magazine 10 by the magnets 20.

Figure 5:
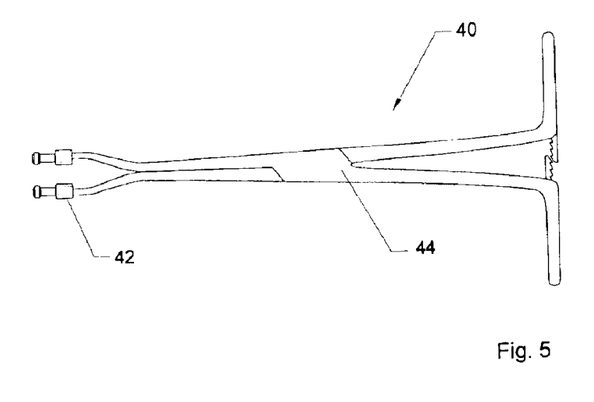
FIG. 5 is a top view of a magazine tongs that is part of the worksite suite of the present invention.
Figure 6:
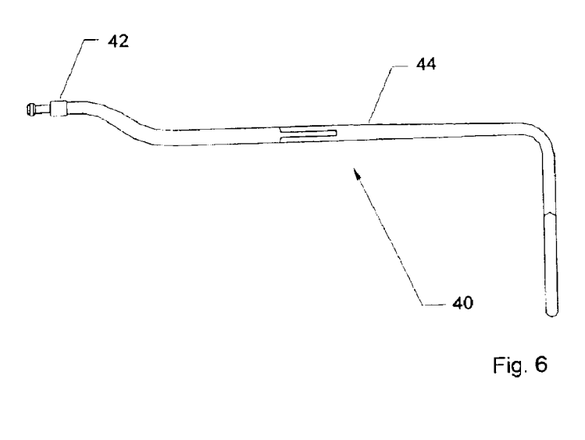
FIG. 6 is a side view of the magazine tongs in FIG. 5.
Figure 7:
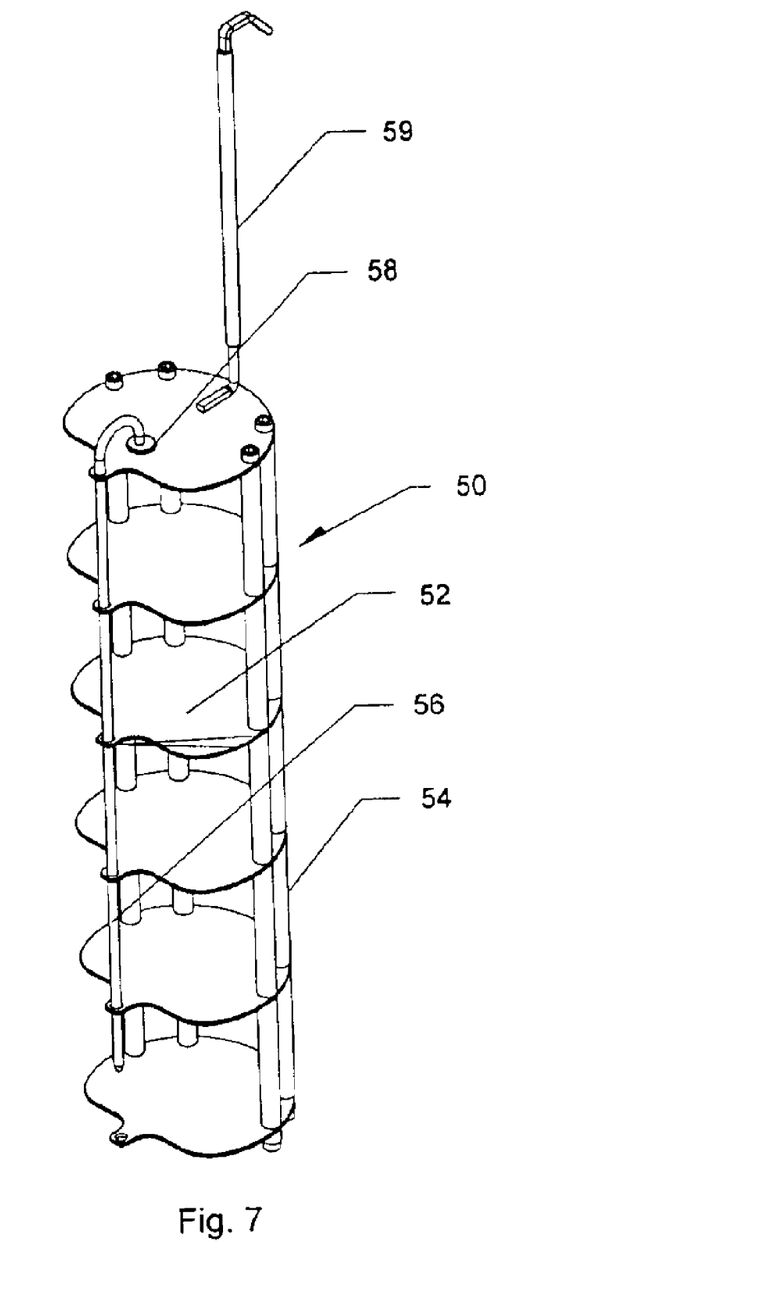
FIG. 7 is a shipping rack that holds five magazines of the present invention.

The magazine 10 is handled using a grasping tool or magazine tongs 40 that utilize a "dumbbell" shaped tip 42 attached to the end of forceps 44 (FIGS. 5 and 6). The tips 42 grasp the magazine 10 via slotted tabs 21 at the top edge of the magazine 10, as shown in FIG. 3. Since the magazine 10 is typically submerged in liquid nitrogen, the magazine tongs 40 allow the user to remove the magazine from one dewar to another. The typical dewar of the prior art has a rack with a number of rack plates each spaced by threaded standoff members. The rack 50 shown in FIG. 7 is designed to be compatible with the magazines 10 and the suite of the present invention thus having six plates 52. The plates 52 are made from martensitic stainless steel that allows the magazine 10 to be held in place by the magnets 20. The threaded standoff members 54 are configured to provide the spacing between plates 52 to place a magazine 10 on each plate 52 and provide a guide for the gross location of the magazine 10 on the plate 52. A retaining bar 56 fits in slot 23 of magazines 10 (FIG. 3) to securely hold the magazine 10 on the plate 52. The retaining bar 56 is held in position by passing through holes in plates 52 and secured by a magnet 58. A support rod 59 is attachable to the top plate 52 to place the five magazines into or remove the magazines from a dewar.

Reference is made to U.S. Pat. Nos. 6,408,047 and 6,494,849, both of which are directed to providing a method of performing x-ray crystallography on samples using a robot or robotic arm. The magazines 10 of the present invention are specially suited and compatible to be used in such a system. The worksite suite of the present invention provides for high volume of crystal samples to be tested while lessening the need for human intervention.

Figure 8:
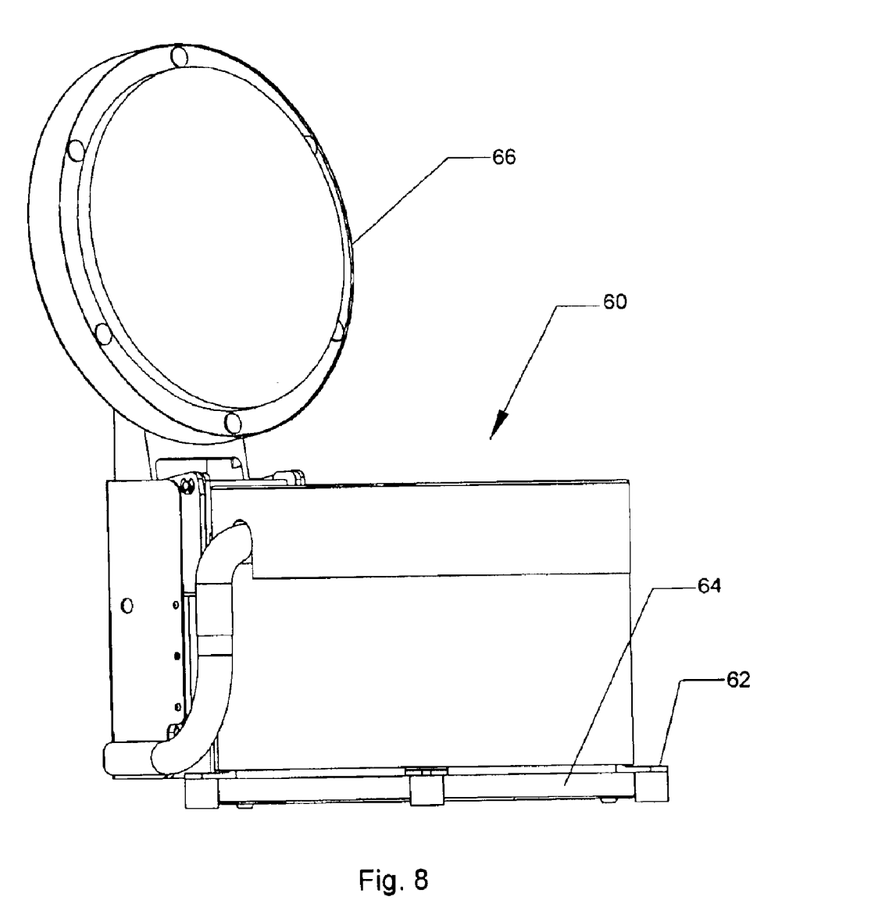
FIG. 8 is a worksite dewar.
Figure 9:
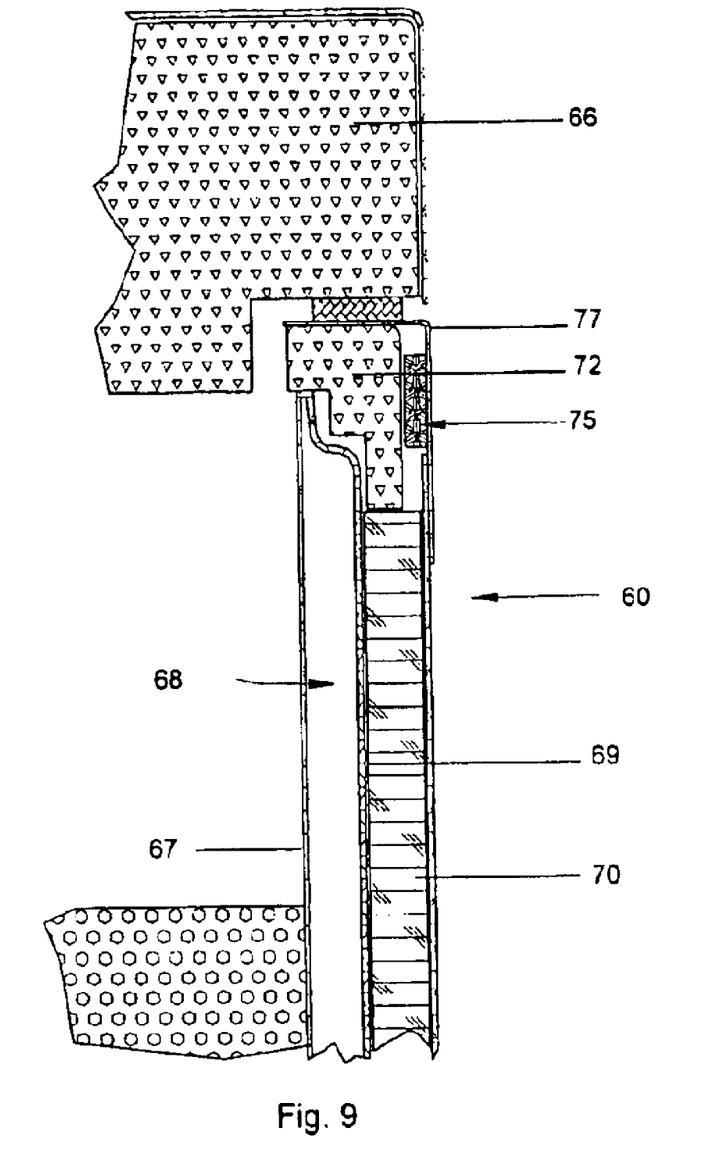
FIG. 9 is a partial cross-section of the dewar.

Another central component of the worksite suite of the present invention is the worksite dewar 60. Now referring to FIG. 8, the worksite dewar 60 provides a staging area for the crystallography system. The dewar 60 is placed in a mounting fixture 62 that is precisely calibrated with the robotic arm of a robot system. A condensation catch pan 64 is at the bottom of the dewar 60. The dewar 60 has a lid 66. The dewar is a double wall flask 68 with a vacuum between inner wall 67 and outer wall 69. The flask 68 is capable of holding liquid nitrogen. On the outside of the flask 68 is insulation 70. At the upper portion of the flask 68 is a rim insulator 72. A heater 75 is mounted to the rim 77 to heat the rim 77 but is insulated from the flask 68. The heater 75 minimizes condensation on the rim and prevents the freezing of any condensation that does form on the rim 77 that would prevent the lid 66 from opening.

Figure 10:
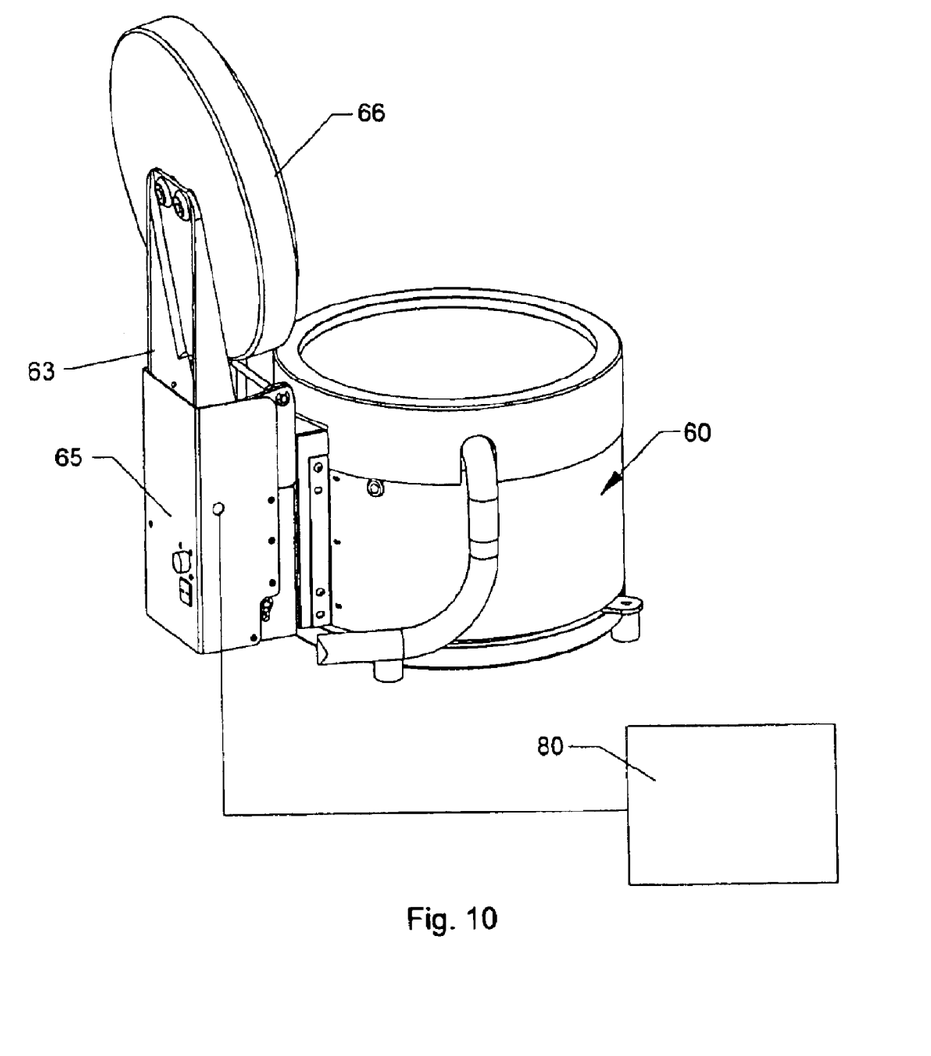
FIG. 10 is the dewar with a programmed controller.
Figure 11:
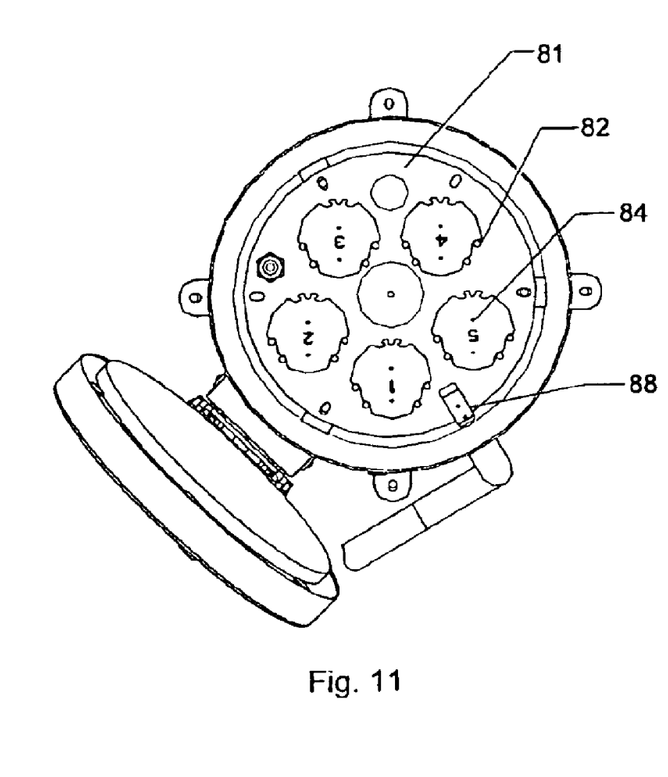
FIG. 11 is a top view of the worksite dewar that has no magazines inside.
Figure 12:
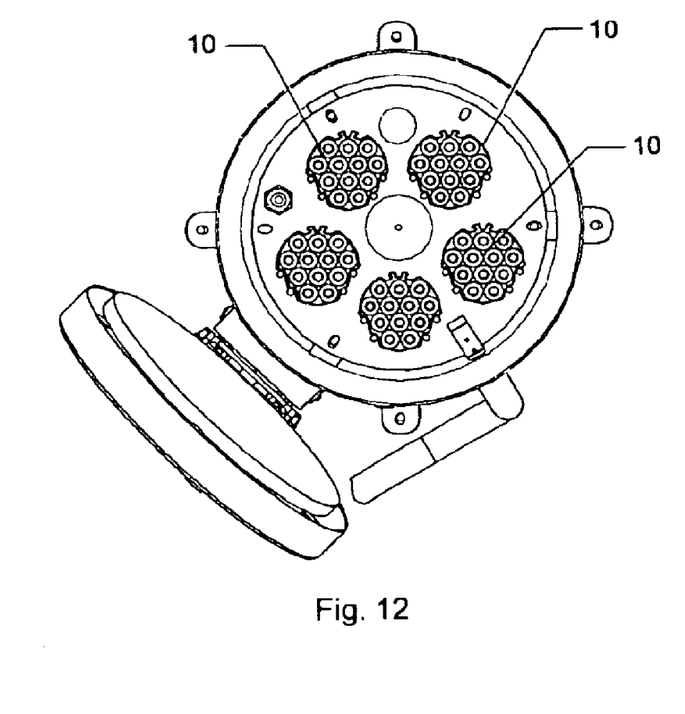
FIG. 12 is a top view of the worksite dewar that has five (5) magazines inside.
Figure 13:
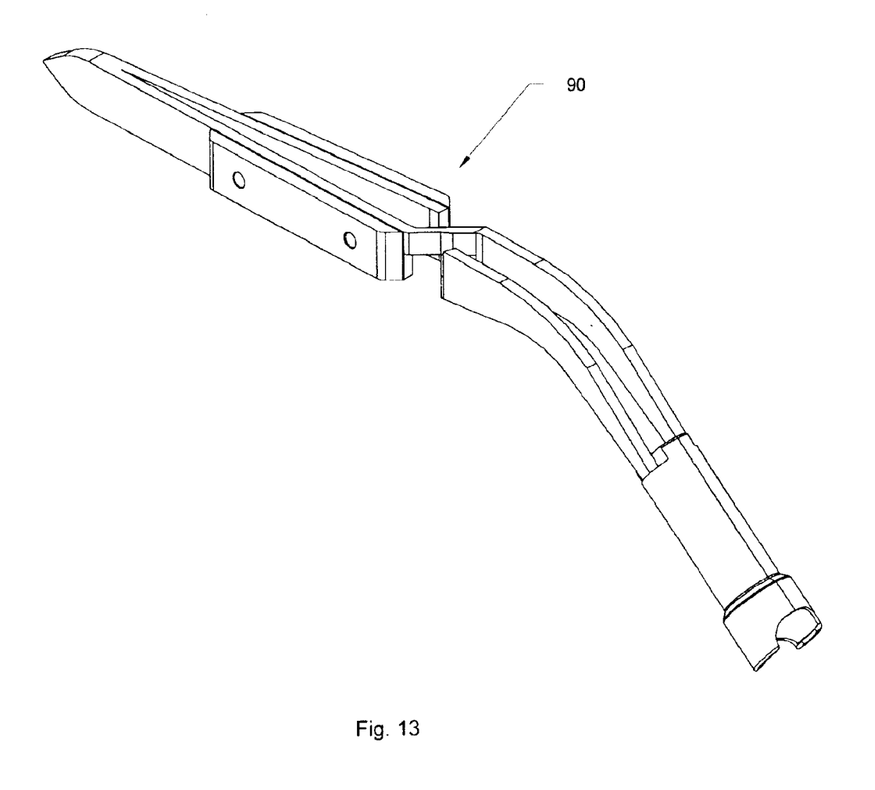
FIG. 13 is a cryo-pin tongs that removes cryo-pins from a magazine manually and is part of the worksite suite of the present invention.

Referring to FIG. 10, the worksite dewar lid actuator assembly 65, is connected to a programmable controller 80 that may be separate from or part of the robot system. The actuator assembly 65 is comprised of a commercial linear actuator attached to the outboard end of the lid hinge 67, beyond the lid hinge pin. The actuator assembly 65 also includes micro switches which provide interlocks for both robot and dewar lid operation. When part of the robot system, the controller 80 will open the lid 66 before the robotic arm enters the dewar 60 to remove or return a crystal to a magazine in the dewar 60. As shown in FIGS. 11 and 12, the worksite dewar 60 holds five magazines 10. The floor of flask 68 has a precision mounting plate 81 which has twenty alignment pins 82, four for each magazine for the course alignment of a magazine 10 and ten alignment pins 84 for the fine alignment of each magazine 10. The dewar 60 has a liquid cryogen, liquid nitrogen, inlet 88 on the side of the dewar 60. As shown in FIG. 12, five magazines 10 are placed in the working dewar 60, containing a total of sixty samples of crystals to be tested by x-ray crystallography.

Pin tongs 90 are part of the suite of the present invention since there are occasions when the cryo-pins 30 are handled manually.

What is claimed is:

1. A worksite system used in crystallography applications comprising:
   a dewar, the dewar further comprising a rim at an upper portion thereof and a heater disposed proximate said rim of said dewar;
   a plurality of magazines which may be placed in said dewar;
   each magazine having a plurality of cylinders, each cylinder adapted to hold a cryo-pin having a crystal mounted thereon; and a cryo-pin tong for removing said cryo-pin and positioning said crystal mounted on said pin in a goniometer.

2. A worksite system used in crystallography applications according to claim 1 wherein said dewar has a top that is adapted to be opened and closed.

3. A worksite system used in crystallography applications according to claim 2 wherein said top is adapted to be opened and closed by a programmed controller.

4. A worksite system used in crystallography applications according to claim 1 wherein said plurality of magazines are adapted to be placed in said dewar simultaneously.

5. A worksite system used in crystallography applications comprising:
   a dewar, the dewar further comprising a rim at an upper portion thereof and a heater disposed proximate said rim of said dewar;
   a programmed controller; and
   a top on said dewar that is opened and closed by said programmed controller.

* * * * *